(12) United States Patent
Umetsu et al.

(10) Patent No.: US 10,379,044 B2
(45) Date of Patent: Aug. 13, 2019

(54) ANALYSIS CHIP AND ANALYSIS APPARATUS

(71) Applicant: Konica Minolta, Inc., Tokyo (JP)

(72) Inventors: Hiroshi Umetsu, Kokubunji (JP); Yoshihiro Okumura, Toyohashi (JP)

(73) Assignee: KONICA MINOLTA, INC., Tokyo (JP)

( * ) Notice: Subject to any disclaimer, the term of this patent is extended or adjusted under 35 U.S.C. 154(b) by 13 days.

(21) Appl. No.: 15/540,472

(22) PCT Filed: Jan. 19, 2016

(86) PCT No.: PCT/JP2016/051466
§ 371 (c)(1),
(2) Date: Jun. 28, 2017

(87) PCT Pub. No.: WO2016/117570
PCT Pub. Date: Jul. 28, 2016

(65) Prior Publication Data
US 2018/0275054 A1    Sep. 27, 2018

(30) Foreign Application Priority Data

Jan. 20, 2015    (JP) .................................. 2015-008292

(51) Int. Cl.
*G01N 21/552* (2014.01)
*G01N 21/41* (2006.01)
(Continued)

(52) U.S. Cl.
CPC ............ *G01N 21/554* (2013.01); *B01L 3/508* (2013.01); *G01N 21/41* (2013.01); *G01N 21/64* (2013.01);
(Continued)

(58) Field of Classification Search
CPC ...... G01N 21/554; G01N 21/41; G01N 21/64; B01L 3/508; B01L 2200/16; B01L 2300/0627
See application file for complete search history.

(56) References Cited

U.S. PATENT DOCUMENTS

| 2006/0146333 A1* | 7/2006 | Hakamata | G01N 21/05 356/445 |
| 2011/0150705 A1 | 6/2011 | Doyle et al. | |
| 2013/0343955 A1* | 12/2013 | Doyle | B01L 3/5055 422/82.02 |

FOREIGN PATENT DOCUMENTS

| JP | 2003344275 A | 12/2003 |
| JP | 2012058053 A | 3/2012 |

(Continued)

OTHER PUBLICATIONS

Written Opinion of the International Searching Authority dated Apr. 19, 2016 from corresponding International Application No. PCT/JP2016/051466 and English translation.

(Continued)

*Primary Examiner* — Dennis White
(74) *Attorney, Agent, or Firm* — Lucas & Mercanti, LLP

(57) ABSTRACT

An analysis chip contains a test reagent retention member and a sensing member. The test reagent retention member has a housing part for housing the sensing member, and an engaging part for engaging the sensing member within the housing part. The sensing member is secured in the housing part by the engaging part, in such a way as to have a certain area of mobility in relation to the housing part.

13 Claims, 15 Drawing Sheets

(51) Int. Cl.
*G01N 21/64* (2006.01)
*B01L 3/00* (2006.01)
(52) U.S. Cl.
CPC ... *B01L 2200/16* (2013.01); *B01L 2300/0627* (2013.01)

(56) References Cited

FOREIGN PATENT DOCUMENTS

| | | | |
|---|---|---|---|
| JP | 2013024607 A | 2/2013 | |
| WO | 2013192289 A1 | 12/2013 | |
| WO | 2014046000 A1 | 3/2014 | |

OTHER PUBLICATIONS

Extended European Search Report dated Feb. 22, 2018 from corresponding European Application No. 16740177.7.
International Search Report dated Apr. 19, 2016 for PCT/JP2016/051466 and English translation.

* cited by examiner

ANALYSIS CHIP AND ANALYSIS APPARATUS

CROSS REFERENCE TO RELATED APPLICATION

This Application is a 371 of PCT/JP2016/051466 filed on Jan. 19, 2016, which, in turn, claimed the priority of Japanese Patent Application No. 2015-008292 filed on Jan. 20, 2015, both applications are incorporated herein by reference.

TECHNICAL FIELD

The present invention relates to an analysis chip and an analysis apparatus, in particular to an analysis chip for analysis using the principle of SPR (Surface Plasmon Resonance).

BACKGROUND ART

In the field of POCT (Point Of Care Testing), analysis chips using SPR (hereinafter referred to as analysis chips) have been actively developed.

Such analysis chips (sensing members or sensor chips) are often formed only from a prism with a metal film (dielectric medium) and a member defining a channel. Sensing members are typically placed in an analysis apparatus that includes a light source and a detector, and the sensing members themselves seldom include a part or member for retaining test reagent (test reagent retention member). In such configurations, a test reagent retention member is often previously incorporated in an analysis apparatus or is separately placed in an analysis apparatus by a user, and a sensing member is placed therein. Since the test reagent retention member and the sensing member are individually handled in this way, preparation for a measurement and cleaning up thereof are likely to be complicated.

In POCT, test reagent retention members and sensing members are often used once and thrown away in terms of work efficiency and safety. Such a process requires a complicated user work since a test reagent retention member and a sensing member are individually disposed. Furthermore, in a test of detecting a biological substance such as protein or DNA, there is a biohazard risk for the user.

In recent years, there has been an increasing need for a chip in which a test reagent retention member is integrated with a sensing member in terms of improving the usability (ease of use) and achieving unified lot management of test reagent retention members and sensing members (management of products with respect to each product unit) which can improve the detection precision by maintaining the relation between the test reagent and the sensing.

Patent Document 1 discloses an example of such integration, in which a plate main body as a test reagent retention member is integrated with a detection chip as a sensing member.

In particular, the technique proposed in Patent Document 1 is such that a detection groove 13 with a V-shaped cross section is formed in the detection chip 11, and an electric field enhancing layer 14 is formed on the surface thereof. With this configuration, surface plasmon is likely to be readily excited (see paragraphs 0044 to 0045, FIG. 7 (*b*), Example 1 and Example 2).

PRIOR ART DOCUMENT

Patent Documents

Patent Document 1: JP 2013-24607A

SUMMARY OF INVENTION

Problem to be Solved by Invention

Patent Document 1 also describes that an accommodating part 4 is formed in a recess shape in the main body plate 2, and the detection chip 8 is accommodated therein (see paragraph 0039 and FIG. 4). Further, in the other part of the document, it merely describes that the accommodating part 104 is formed in the main body plate 2, and the detection chip 108 is accommodated therein (see paragraph 0042 and FIG. 6), and that a cylindrical accommodating part 104 is formed in the main body plate 2, and a cylindrical detection chip 71 is embedded therein (see paragraphs 0065 to 0066 in Example 2). Patent Document 1 does not describe about integration of a test reagent retention member with a sensing member. Since there is a possibility of separation of these members during product delivery or user work, the technique cannot be suitable for lot management for improving the detection precision.

Another problem with currently-used analysis chips is as follows.

While analysis apparatuses using SPR are based on optical detection using an excitation light and therefore have high detection precision, high precision is required in positioning of a sensing member in an analysis apparatus. Particularly when an immobilized membrane of a sensing member, which is a metal film with an analyte immobilized thereon, is adjusted approximately to the size of excitation light in order to improve the detection precision, or when SPFS (Surface Plasmon-field enhanced Fluorescence Spectroscopy) is used for sensitive detection, very high precision of approximately ±50 μm or less from a reference position is required in positioning of a sensing member in an analysis apparatus.

In this regard, since disposable items are often used in POCT, test reagent retention members are often made of PP (polypropylene) in consideration of the resistance to test reagents and the cost. Crystalline resins such as PP have poor shape precision since warpage is easily caused due to the properties and also have poor dimension precision due to the high shrinkage ratio in molding. That is, crystalline resins have poor shape and dimension precision. Accordingly, if such a test reagent retention member is integrated with a sensing member by means of fusion or press fitting for lot management, it would be difficult to carry out precise positioning of a sensing member in an analysis apparatus.

An attempt to improve the shape and dimension precision of PP for solving this problem would result in the increased production cost due to the difficulty in molding. Since disposable items are often used in POCT, an increase of the production cost is unfavorable. Even when test reagent retention members are made of a non-crystalline resin such as PS (polystyrene) or PC (polycarbonate) which has good shape and dimension precision, it will also result in the increased production cost due to the material price, which is unfavorable.

Therefore, it is a main object of the present invention to provide an analysis chip that can improve the positioning precision of a sensing member in an analysis apparatus while preventing separation of a test reagent retention member from the sensing member.

Means for Solving Problem

In order to solve the above problem, according to the present invention, there is provided an analysis chip for analysis using principle of surface plasmon resonance, including:
a test reagent retention member; and
a sensing member,
wherein the test reagent retention member includes:
a housing part in which the sensing member is housed; and
an engaging part which engages with the sensing member in the housing part, and
wherein the sensing member is housed in the housing part by means of the engaging part with a certain movable area between the sensing member and the housing part.

"To engage" means that the test reagent retention member and the sensing member are detachable from each other only when an external force is applied to the engaging part, and that the regent retention member is not separated from the sensing member but integrated therewith as long as no external force is applied.

Advantageous Effects of Invention

According to the present invention, since the sensing member is secured in the housing part of the test reagent retention member by means of the engaging part of the test reagent retention member, it is possible to prevent the test reagent retention member from being separated from the sensing member.

In particular, since the sensing member has a certain movable area between the sensing member and the housing part, the position of the sensing member is not restricted by the test reagent retention member. It is therefore possible to improve the positioning precision of the sensing member in the analysis apparatus.

Further, since the test reagent retention member and the sensing member are integrated with each other, a sensing member is linked to a test reagent retention member that is used along with the sensing member, which also improves the usability.

BRIEF DESCRIPTION OF THE DRAWING

FIG. 10 C is a side view of the schematic configuration of the presser member.

EMBODIMENTS FOR CARRYING OUT INVENTION

Figure 1:
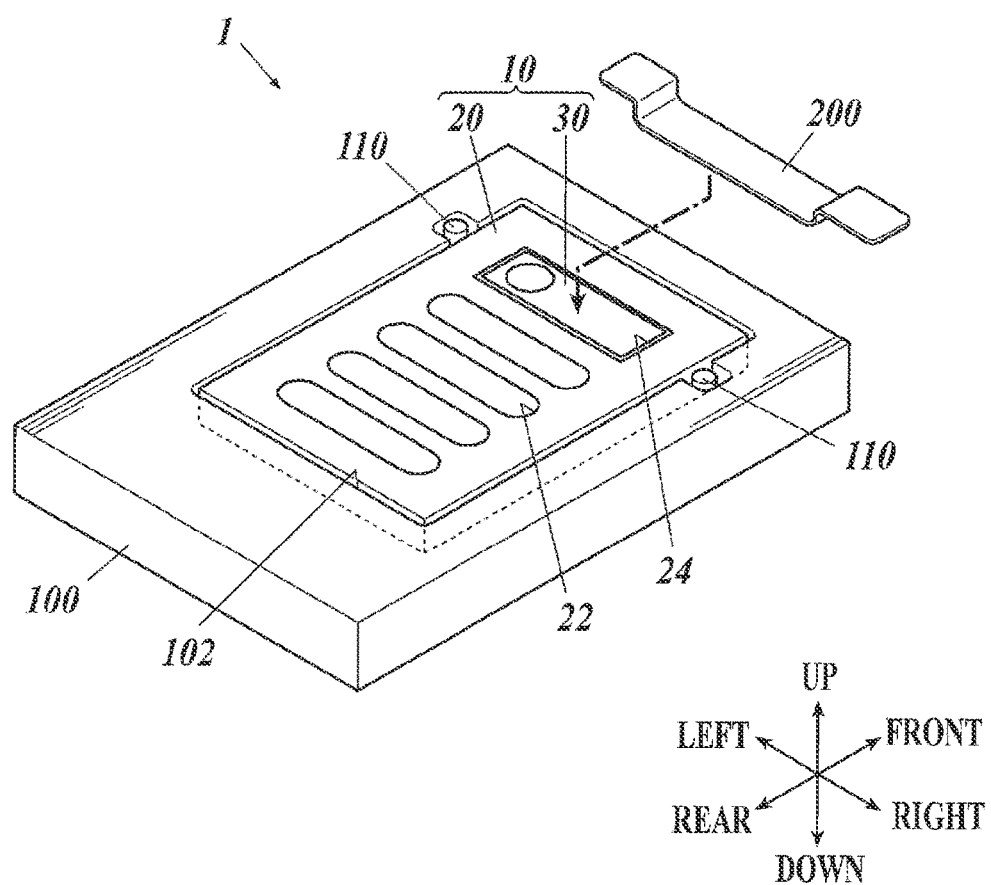
FIG. 1 is a perspective view illustrating the schematic configuration of a chip mounting stage in an analysis apparatus.

Next, a preferred embodiment of the present invention will be described referring to the drawings.

The symbol "-" indicating a numerical range is intended to mean that the lower and upper limits before and after the symbol are included in the numerical range.

Analysis Apparatus

As illustrated in FIG. 1, an analysis apparatus 1 includes an analysis chip 10, a stage 100 and a presser member 200.

In the stage 100, a recess housing part 102 is formed.

In the analysis apparatus 1, the analysis chip 10 is housed in the housing part 102, and the presser member 200 is disposed on the stage 100.

In FIG. 1, the stage 100 and the housing part 102 have respectively a cuboid shape and a rectangular frame shape.

However, the stage 100 and the housing part 102 may have any shape that can house the analysis chip 10.

The analysis chip 10 includes a test reagent retention member 20 a sensing member 30.

In FIG. 1, right, left, up, down, front and rear indicate the directions with reference to the analysis chip 10. The right-left direction indicates the width direction of the analysis chip 10, the up-down direction indicates the height direction of the analysis chip 10, and the front-rear direction indicates the longitudinal direction of the analysis chip 10.

Analysis Chip (Test Reagent Retention Member)

The test reagent retention member 20 is constituted by a test reagent retention container that has approximately a cuboid shape. The test reagent retention member 20 may have any outer shape but preferably has a cuboid shape in terms of ease of handling in mounting to the stage 100 and ease of holding.

In the test reagent retention member 20, recess wells 22 are formed to retain and reserve test reagent. In the test reagent retention member 20, a rectangular frame housing part 24 is also formed. The housing part 24 is provided to house the sensing member 30.

Figure 2A:
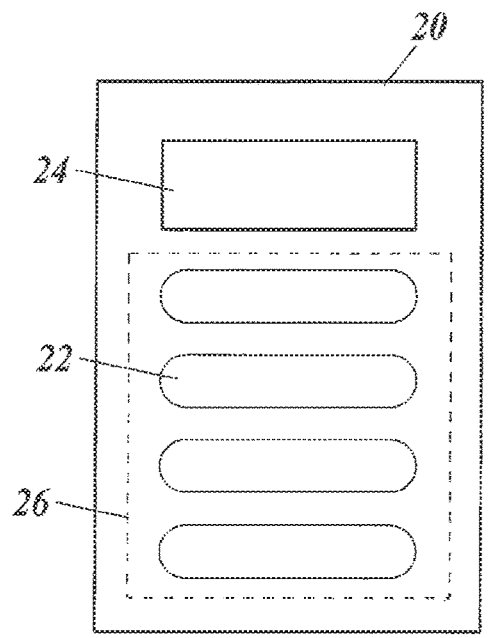
FIG. 2A is a plan view illustrating the schematic configuration of a test reagent retention member.

As illustrated in FIG. 1 and FIG. 2A, four approximately oval wells 22 are formed over the rear part to the center part, and the housing part 24 is disposed in the front part.

The test reagent retention member 20 is made of a glass or resin material.

The test reagent retention member 20 is preferably made of a resin material.

The test reagent retention member may be made of either crystalline resin or non-crystalline resin but is preferably made of a crystalline resin in terms of production cost and resistance to test reagents. For example, the test reagent retention member is preferably made of PP.

It should be noted that the shape and dimension precision of PP is relatively poor, and it is therefore difficult to improve the positioning precision of the test reagent retention member 20 on the stage 100 in the analysis apparatus 1. However, since high precision is not required in positioning of the test reagent retention member 20 in the analysis apparatus 1 as described below, the test reagent retention member 20 of PP does not cause any practical problem.

The shape, the number and the arrangement of the wells 22 are not limited and may be changed. Further, the shape and the arrangement of the housing part 24 are not limited and may be changed.

Figure 2B:
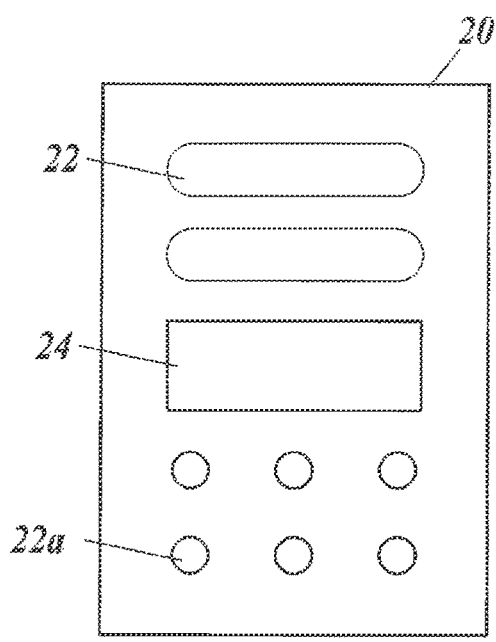
FIG. 2B is a plan view of a variation of the test reagent retention member.
Figure 2C:
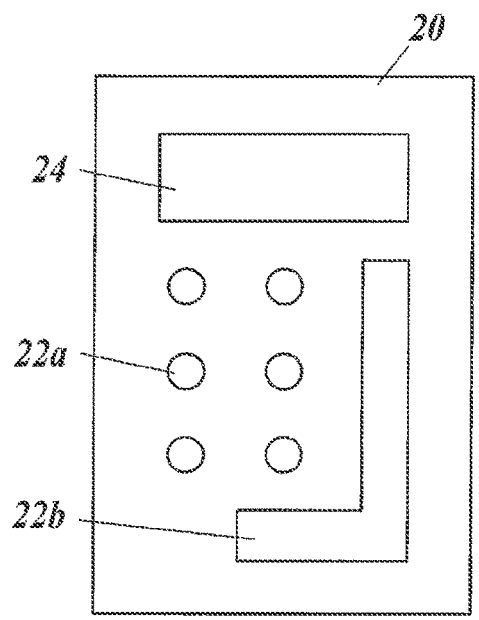
FIG. 2C is a plan view of a variation of the test reagent retention member.
Figure 2D:
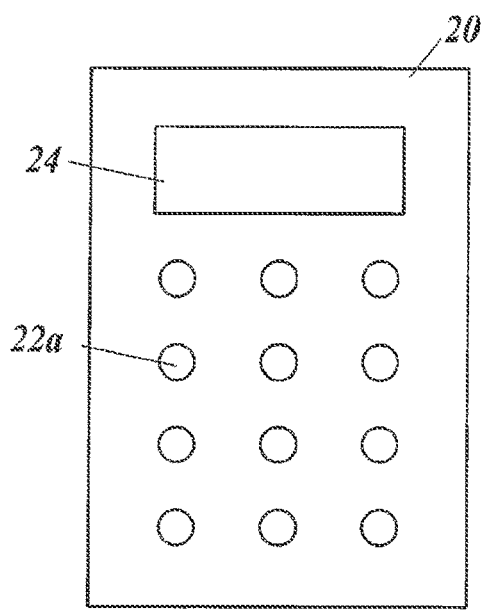
FIG. 2D is a plan view of a variation of the test reagent retention member.

For example, as illustrated in FIG. 2B, six circular wells 22a may be disposed in the rear part as well as two wells 22 in the front part, and the housing part 24 may be disposed in the center part. Alternatively, as illustrated in FIG. 2C, six circular wells 22a and a flipped L-shaped well 22b may be disposed over the rear part to the center part, and the housing part 24 may be disposed in the front part. Alternatively, as illustrated in FIG. 2D, only many circular wells 22a may be disposed over the rear part to the center part, and the housing part 24 may be disposed in the front part.

As illustrated in FIG. 2A, the wells 22 (including the wells 22a and the well 22b) may be sealed with a sealing member 26 in terms of securing the biosafety.

The sealing member 26 may be constituted by any material that allows the test reagent to be collected. The sealing member 26 may be constituted by a PCR sheet or an Al sheet. As for the sealing method, any method that does not affect the test reagent in the wells 22 may be employed. Such sealing methods include thermal fusion and chemical bonding.

Analysis Chip (Sensing Member)

As illustrated in FIG. 1, the sensing member 30 is housed in the housing part 24 of the test reagent retention member 20.

Figure 3A:
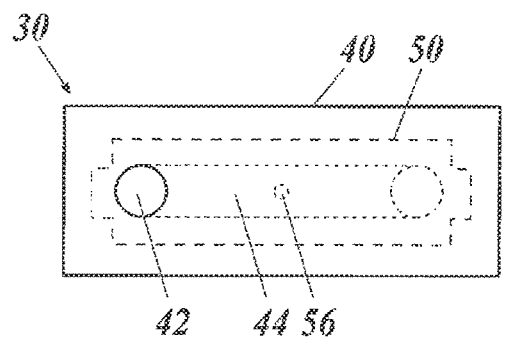
FIG. 3A is a plan view illustrating the schematic configuration of a sensing member.
Figure 3B:
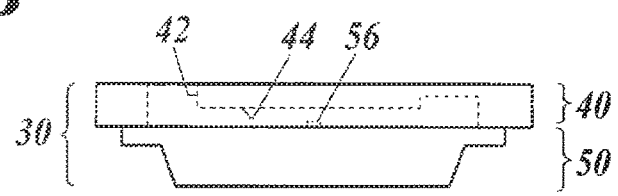
FIG. 3B is a side view illustrating the schematic configuration of the sensing member.

As illustrated in FIG. 3A and FIG. 3B, the sensing member 30 includes a channel member 40 and a prism member 50.

The channel member 40 includes a test reagent introduction part 42 and a reaction channel 44. The test reagent introduction part 42 is a circular through hole. The reaction channel 44 is a space that is formed when the channel member 40 is joined to the prism member 50. The test reagent introduction part 42 and the reaction channel 44 are communicated with each other.

Figure 3C:
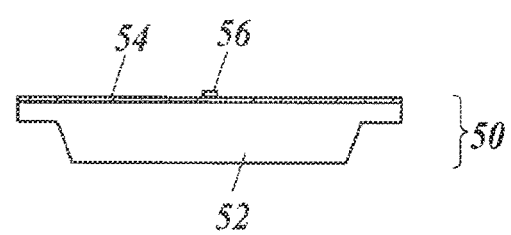
FIG. 3C is a side view illustrating the schematic configuration of a prism member.
Figure 3D:
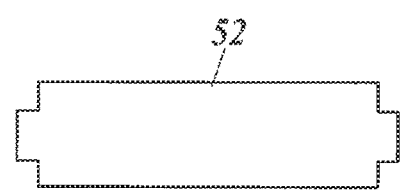
FIG. 3D is a plan view illustrating the schematic configuration of the prism.

As illustrated in FIG. 3C, the prism member 50 includes a prism 52, a metal film 54 and an immobilized membrane 56. The metal film 54 is formed on the prism 52, and the immobilized membrane 56 is formed on the metal film 54. An analyte is immobilized on the immobilized membrane 56.

The channel member 40 and the prism 52 are made of a glass or resin material.

It is preferred that the channel member 40 and the prism 52 are made of a material that is different from the material of the test reagent retention member 20. More preferably, they are made of glass, which has good shape and dimension precision, or a material that is different from the material of the test reagent retention member 20 and has better shape and dimension precision than the material of the test reagent retention member 20.

Since the channel member 40 and the prism 52 have to be transparent for optical detection, the channel member 40 and the prism 52 are preferably made of glass or a non-crystalline resin. For example, it is preferred that the channel member 40 is made of PMMA (polymethyl methacylate acryl), and the prism 52 is made of COP (cycloolefin polymer).

Since PMMA and COP have better shape and dimension precision than PP that can be the material of the test reagent retention member 20, the shape and dimension of the channel member 40 and the prism 52 are closer to their designed values compared to the test reagent retention member 20.

Integration of Test Reagent Retention Member and Sensing Member

The test reagent retention member 20 is integrated with the sensing member 30 in a snap-fitting manner.

Figure 4A:
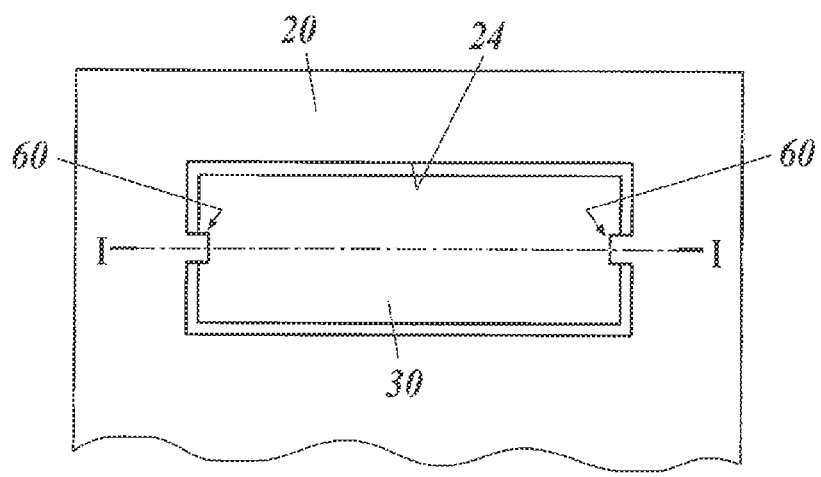
FIG. 4A is a plan view illustrating the schematic configuration of the vicinity of a housing part of the test reagent retention member.

As illustrated in FIG. 4A, a pair of snap-fitting engaging parts 60 are formed in the housing part 24 of the test reagent retention member 20. The engaging parts 60 may be made of the same or different material from the test reagent retention member 20. In terms of productivity, it is preferred that the engaging parts 60 are made of the same material as the test reagent retention member 20. When the test reagent retention member 20 is made of PP, this configuration makes the engaging parts 60 particularly suitable for snap-fitting since PP is a relatively soft material.

Figure 4B:
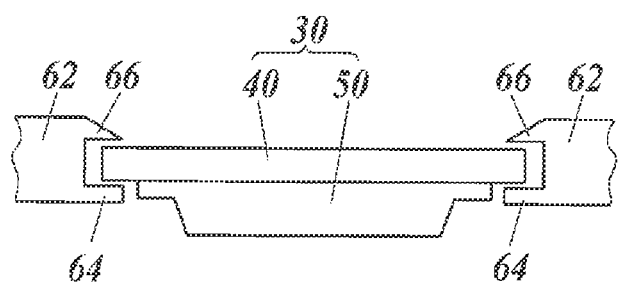
FIG. 4B is a schematic cross-sectional view taken along the line I-I in FIG. 4A.

As illustrated in FIG. 4B, the engaging parts 60 include inner walls 62, supports 64 and hooks 66. The engaging parts 60 are structurally symmetrical in the right-left direction. The supports 64 protrude from the lower parts of the inner walls 62. The hooks 66 protrude from the upper parts of the inner walls 62.

The sensing member 30 are held between the supports 64 and the hooks 66 and thus housed in the housing part 24.

In this configuration, certain movable areas (gaps) are formed between the housing part 24 of the test reagent retention member 20 and the sensing member 30.

The movable areas are formed in all directions of the right-left, up-down and front-rear directions.

The movable areas in the right-left direction are formed between the inner walls 62 and the channel member 40.

The movable areas in the up-down direction are formed between the hooks 66 and the channel member 40.

Figure 11A:
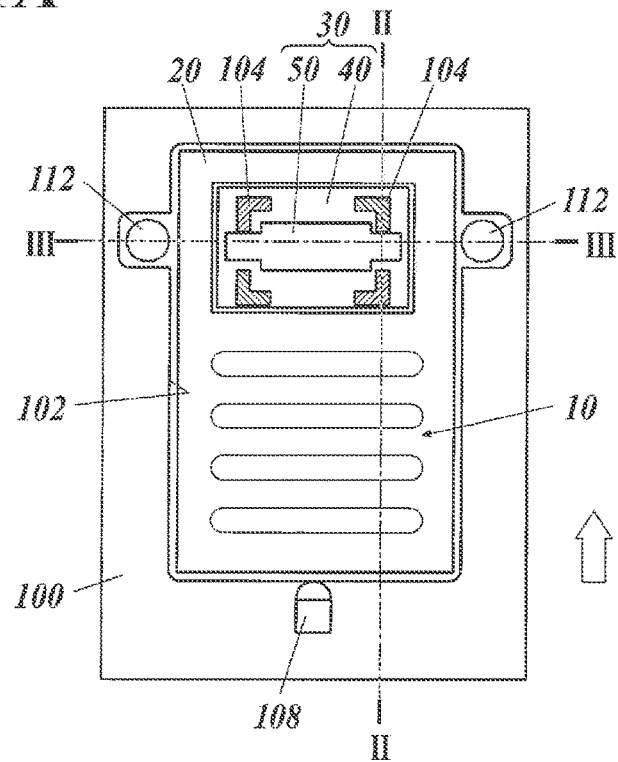
FIG. 11A is a plan view illustrating the state in which an analysis chip is mounted on a stage.
Figure 11B:
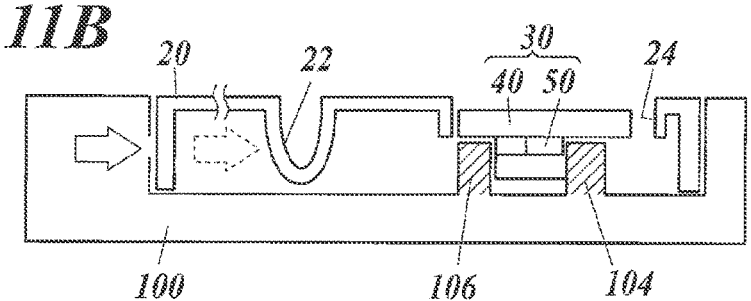
FIG. 11B is a schematic cross-sectional view taken along the line II-II in FIG. 11A.

The movable areas in the front-rear direction are formed between the front and rear inner walls of the housing part 24 and the channel member 40 (see FIG. 11B).

Figure 5A:
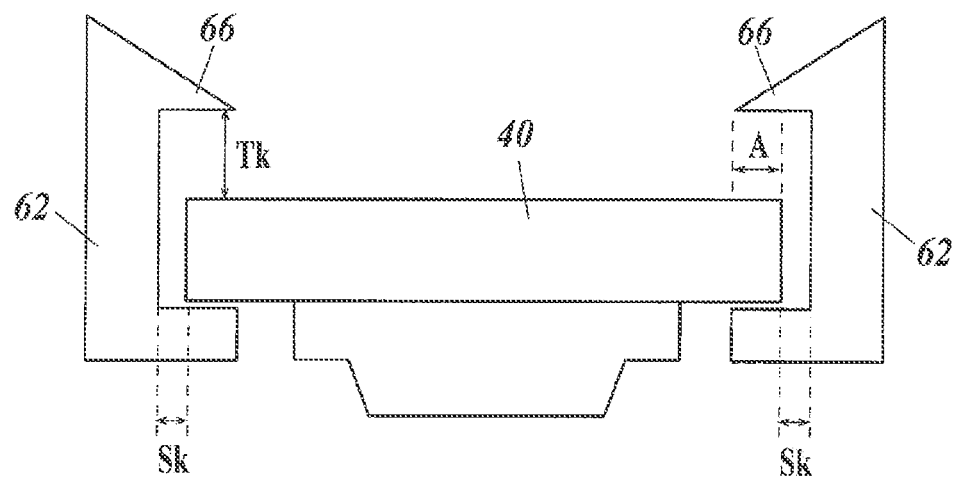
FIG. 5A illustrates movable areas between the test reagent retention member and the sensing member.

As illustrated in FIG. 5A, the movable areas Sk in the right-left direction between the inner walls 62 and the channel member 40 satisfy the condition of the expression (1), preferably the condition of the expression (1a).

$$0.01 \leq Sk \leq 0.58\text{mm} \tag{1}$$

$$0.03 \leq Sk \leq 0.58\text{mm} \tag{1a}$$

In the expression (1), the lower limit corresponds to the processing precision limit of the test reagent retention member 20. The upper limit is derived from the following reason.

Figure 5B:
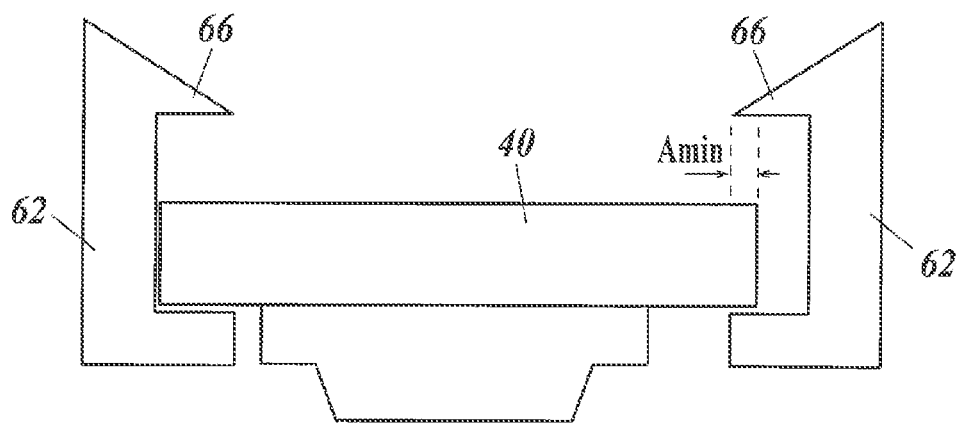
FIG. 5B illustrates movable areas between the test reagent retention member and the sensing member.

When the channel member 40 is disposed at the center between the hooks 66 as illustrated in FIG. 5A, the engaging distance A between the hooks 66 and the channel member 40 has to be equal to or less than 0.7 mm in order to maintain the engagement of the engaging parts 60 with the sensing member 30. When the channel member 40 is deviated so that one end thereof is aligned with an inner wall 62 as illustrated in FIG. 5B, the minimum engaging distance Amin (=A-Sk) between a hook 66 and the channel member 40 has to be equal to or greater than 0.12 mm.

Considering both of the conditions, the upper limit of the movable areas Sk is calculated as 0.7 mm-0.12 mm=0.58 mm.

The movable areas Tk in the up-down direction between the hooks 66 and the channel member 40 satisfy the condition of the expression (2), preferably the condition of the expression (2a).

$$0.01 \leq Tk \leq 1\text{mm} \tag{2}$$

$$0.03 \leq Tk \leq 1\text{mm} \tag{2a}$$

In the expression (2), the lower limit corresponds to the processing precision limit of the test reagent retention member 20. The upper limit corresponds to the limit in which the engagement between the engaging parts 60 and the sensing member 30 is not released but maintained even when one end of the channel member 40 is aligned with an inner wall 62 and lifted.

The engaging parts 60 may have any shape, arrangement or the like that satisfies the expressions (1), (1a), (2) and (2a). Further, the configuration of the engaging parts 60 is not limited to the snap-fitting type and may be changed.

Figure 6A:
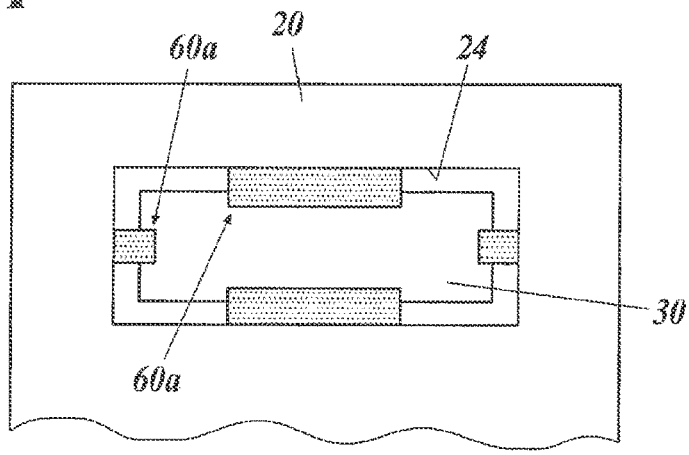
FIG. 6A is a plan view of a variation of an engaging part.
Figure 6B:
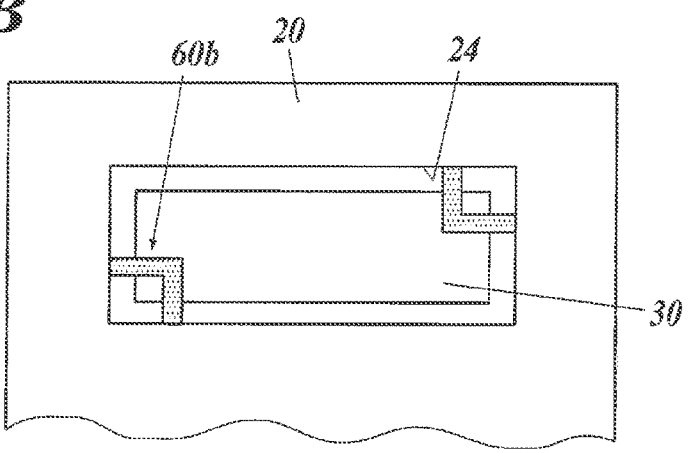
FIG. 6B is a plan view of a variation of the engaging part.
Figure 6C:
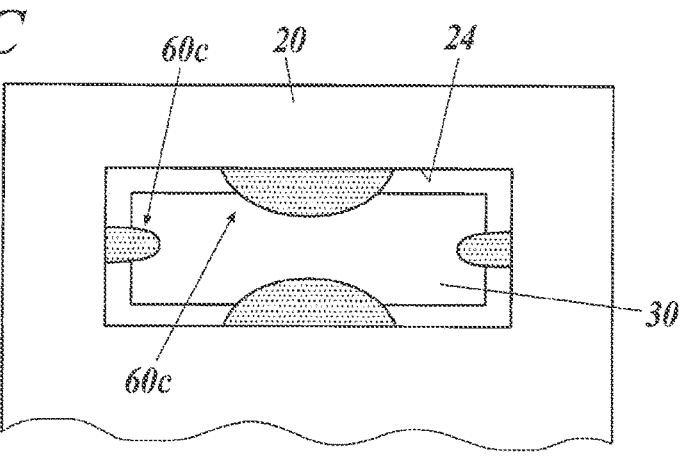
FIG. 6C is a plan view of a variation of the engaging part.

For example, as illustrated in FIG. 6A, engaging parts 60*a* having a rectangular shape in a plan view may be formed in four parts of the front, rear, right and left parts of the housing part 24. Alternatively, as illustrated in FIG. 6B, engaging parts 60*b* having an L shape in a plan view may be formed in corners of the housing parts 24. Alternatively, as illustrated in FIG. 6C, engaging parts 60*c* having an approximately semi-circular shape in a plan view may be formed in four parts of the front, rear, right and left parts of the housing part 24.

Figure 7A:
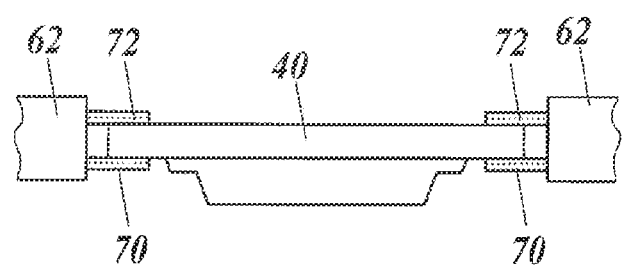
FIG. 7A is a schematic cross-sectional view of a variation of the engaging part.
Figure 7B:
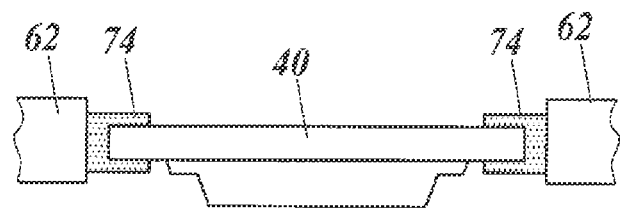
FIG. 7B is a schematic cross-sectional view of the variation of the engaging part.

In such configurations, supports 70 and hooks 72 that are independent from the inner wall 62 are provided on the inner wall 62 to hold the channel member 40 between them as illustrated in FIG. 7A. Alternatively, as illustrated in FIG. 7B, U-shaped holders 74 that are independent from the inner wall 62 may be provided to hold the channel member 40 in it. The supports 70, the hooks 72 and the holders 74 may be preferably made of an elastic material such as rubber or sponge.

Figure 8A:
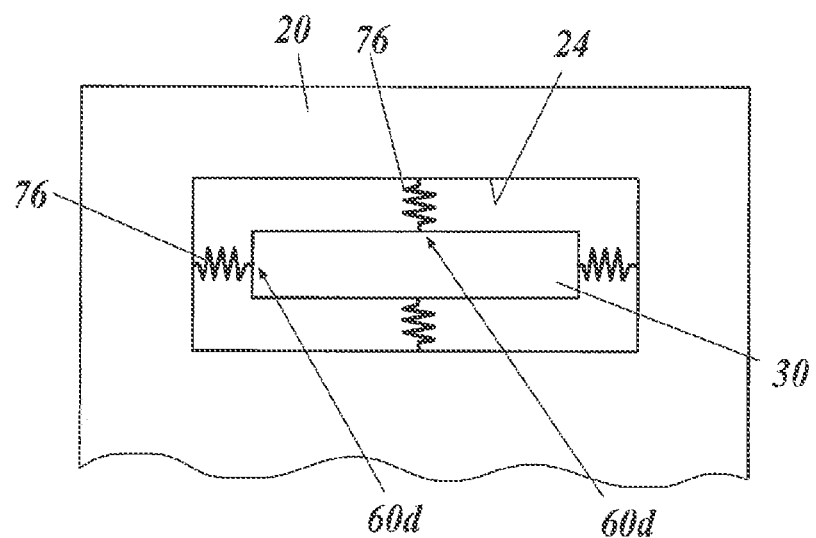
FIG. 8A is a plan view of a variation of the engaging part.

Alternatively, as illustrated in FIG. 8A, spring engaging parts 60*d* using springs 76 may be formed in four parts of the front, rear, right and left parts of the housing part 24.

Figure 8B:
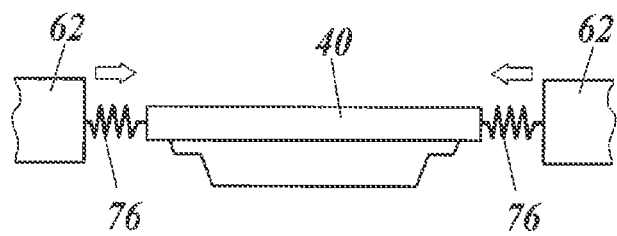
FIG. 8B is a schematic cross-sectional view of the variation of the engaging part.

In this configuration, as illustrated in FIG. 8B, the springs 76 are provided on the inner wall 62 to bias the channel member 40 in the pressing direction so as to hold the channel member 40 between them. The springs 76 may be constituted by resin springs, metal springs or ceramic springs.

Figure 9A:
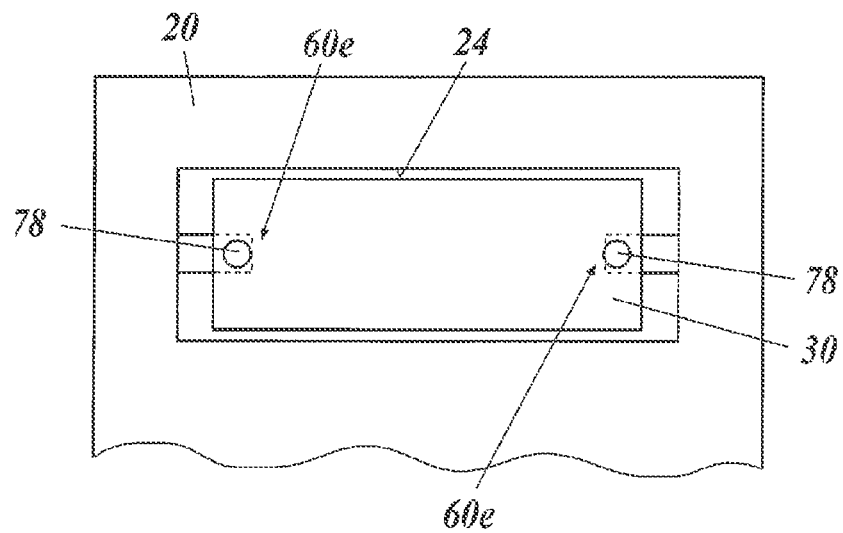
FIG. 9A is a plan view of a variation of the engaging part.

Alternatively, as illustrated in FIG. 9A, press-fitting engaging parts 60*e* may be formed. The engaging parts 60*e* may also be made of the same or different material from the test reagent retention member 20. In terms of productivity, it is preferred that the engaging parts 60*e* are also made of the same material as the test reagent retention member 20.

Figure 9B:
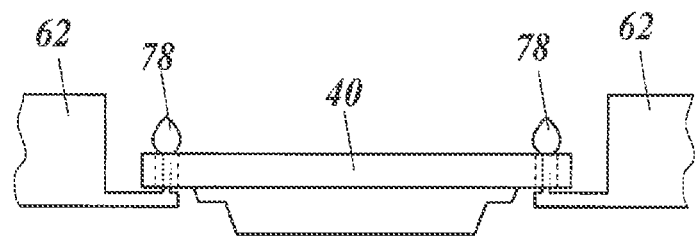
FIG. 9B is a schematic cross-sectional view of the variation of the engaging part.

In this configuration, hooks 78 are formed on the inner wall 62 integrally with the inner wall 62, which are inserted through the channel member 40 as illustrated in FIG. 9B.

In terms of cost and workability, it is preferred to employ the snap-fitting method for the integration of the test reagent retention member 20 with the sensing member 30.

Stage and Presser Member

Figure 10A:
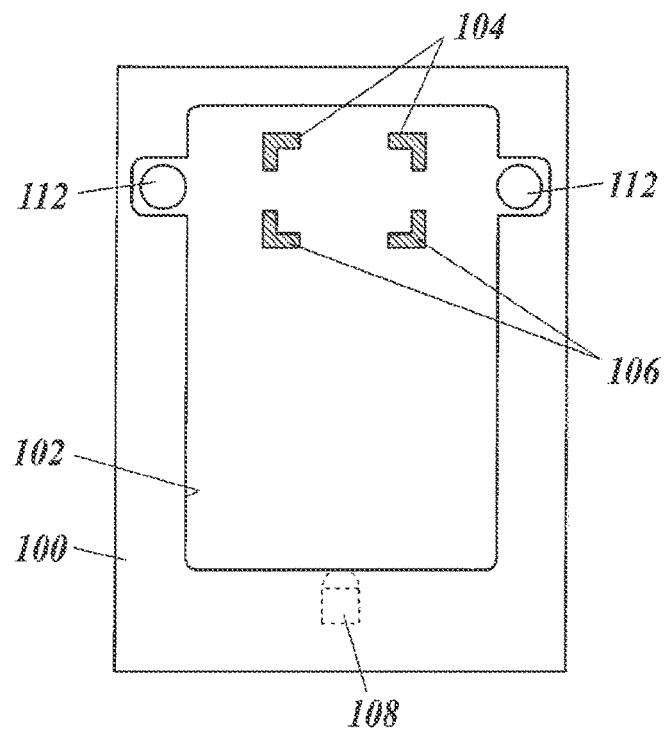
FIG. 10A is a plan view illustrating the schematic configuration of a stage in an analysis apparatus on which a chip is to be mounted.

As illustrated in FIG. 10A, protrusions 104, 106 having an L shape in a plan view are formed in a housing part 102 of a stage 100. Between the front protrusions 104 and the rear protrusions 106, gaps are formed so that the prism member 50 can be housed.

A plunger 108 is provided to the rear of the protrusions 104, 106. The plunger 108 is provided inside the case of the stage 100.

As illustrated in FIG. 11A, when the analysis chip 100 is housed in the housing part 102, the prism member 50 is housed between the protrusions 104 and the protrusions 106. At the same time, the plunger 108 presses the outer wall of the test reagent retention member 20 frontward.

Then, as illustrated in FIG. 11B, the pressing force of the plunger 108 is transmitted to the sensing member 30 via the test reagent retention member 20, and the right and left ends of the prism member 50 abuts the protrusions 104. As a result, the sensing member 30 is restricted from moving in the front-rear direction, and the positioning in the front-rear direction of the sensing member 30 is thereby achieved.

In this configuration, the protrusions 104 and the plunger 108 constitute a front-rear positioning member for the sensing member 30.

The arrangement, the number and the pressing position of the presser of the test reagent retention member 20 are not limited and may be changed.

As illustrated in FIG. 11B, the presser may be disposed inside the test reagent retention member 20 to press the outer wall of the wells 22. Alternatively, unless any disadvantage for the detection is caused, the presser may be disposed inside the case of the stage 100 at the side where the sensing member 30 is disposed, and the positioning in the front-rear direction of the sensing member 30 is achieved by pressing the test reagent retention member 20 to make the ends of the prism member 50 abut the protrusion 106.

The presser may also be changed.

Pressers that can be used include a solenoid, an actuator and an air cylinder. The presser may be constituted by any component that can press the sensing member 30 for a distance longer than the length in the front-rear direction of the movable areas.

As illustrated in FIG. 10A, cylindrical protrusions 112 are formed respectively on the right and left of the protrusions 104, 106. The tops of the protrusions 112 are constituted by magnets.

Figure 10B:
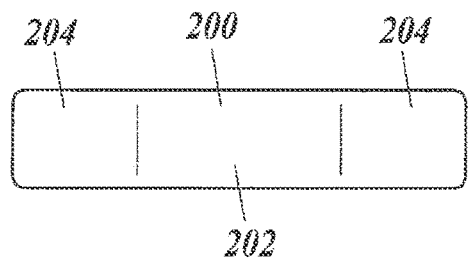
FIG. 10 B is a plan view of the schematic configuration of a presser member.
Figure 10C:
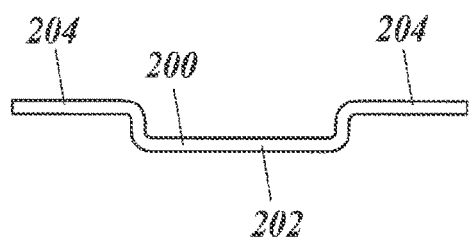

As illustrated in FIG. 10B and FIG. 10C, the presser member 200 is constituted by a metal plate with a certain thickness. The presser member 200 has a recess in the center part, and the presser member 200 includes a bottom part 202 and top plate parts 204 that are connected to each other.

Figure 11C:
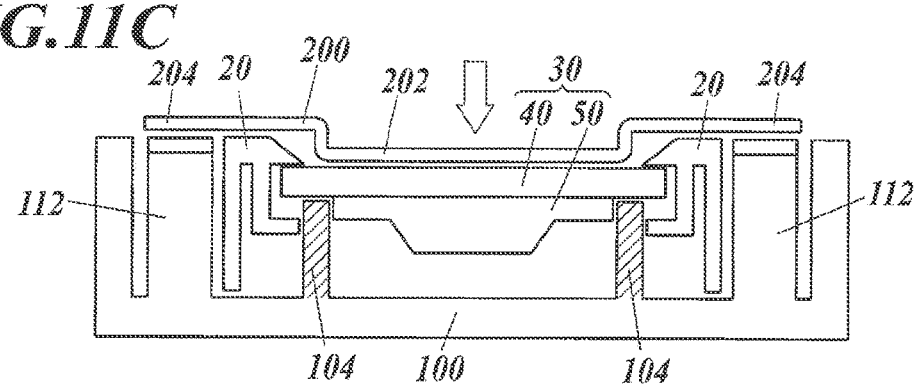
FIG. 11C is a schematic cross-sectional view taken along the line in FIG. 11A.

As illustrated in FIG. 11C, when the presser member 200 is placed on the top of the stage 100, the top plate parts 204 stick to the protrusions 112 by the magnetic force so that the presser member 200 presses the channel member 40 downward.

Then, the pressing force of the presser member 200 is transmitted to the sensing member 30 via the bottom part 202, and the under face of the channel member 40 abuts the top faces of the protrusions 104, 106. As a result, the sensing member 30 is restricted from moving in the up-down direction, and the positioning in the up-down direction of the sensing member 30 is thereby achieved.

In this configuration, the protrusions 104, 106, the protrusions 112 and the presser member 200 constitute an up-down positioning member of the sensing member 30.

The pressing manner is not limited to the above-described manner and may be changed.

An elastic body may be intervened between the sensing member 30 and the presser member 200 so that the sensing member 30 is indirectly pressed.

Further, the presser is not limited to magnetic force and may be changed.

Pressers that can be used include a plunger, a solenoid, an actuator and an air cylinder. The presser may be constituted by any component that can press the sensing member 30 for a distance longer than the length in the up-down direction of the movable areas.

Alternatively, the positioning in the up-down direction of the sensing member 30 may be achieved by providing a suction mechanism to the protrusions 104, 106 and suctioning the channel member 40.

In the embodiment, since the sensing member 30 is engaged with the engaging parts 60 and is housed in the housing part 24, it is possible to prevent separation of the test reagent retention member 20 from the sensing member 30. With this configuration, since the test reagent retention member 20 is integrated with the sensing member 30 without causing separation, it is possible to achieve lot management of these members while maintaining the relationship between them. Further, since these members are integrated with each other, it is possible to improve the user workability, the ease of handling and the biosafety.

Since the integration is achieved only by placing the channel member 40 between the supports 64 and hooks 66, the analysis chip 10 is readily assembled.

Regarding the production of the test reagent retention member 20 and the sensing member 30, since they can be individually produced as separate components, a complicated mechanism (molding) that is tailored to both members is not required. This ease of production makes it possible to suppress the cost and to improve the processing precision of the members.

In particular, the analysis chip 10 is configured such that the sensing member 30 is housed in the housing part 24 with a certain movable area between them. When placing the analysis chip 10 in the analysis apparatus 1, it is possible to carry out fine adjustment of the position in the front-rear direction and the up-down direction of the sensing member 30 within the movable area by adjusting the abutting part (protrusions 104, 106) of the stage 100. Therefore, it is possible to improve the positioning precision of the sensing member 30 in the analysis apparatus 1.

In particular, even when the immobilized membrane 56 is adjusted approximately to the size of the excitation light in order to improve the detection precision or when SPFS is used, very high precision of approximately ±50 μm or less with respect to the reference position can be achieved in the positioning in the front-rear direction and the height direction of the sensing member 30 in the analysis apparatus 1.

As described above, the embodiment employs a configuration that improves the positioning precision of the sensing member 30 in the analysis apparatus 1. In contrast, the test reagent retention member 20 does not require such high positioning precision in the analysis apparatus 1 as the sensing member 30, and it is not necessary to carry out such precise positioning as in the sensing member 30. Therefore, as long as the sensing member 30 (channel member 40 and prism 52) is produced from a non-crystalline resin or the like that has high shape and dimension precision, the test reagent retention member 20 can be produced from a crystalline resin or the like that has common shape and dimension precision. Therefore, it is possible to suppress the production cost.

The sensing member 30 is preferably made of glass or a non-crystalline resin that has good shape and dimension precision since it requires high positioning precision in the analysis apparatus 1. In contrast, the test reagent retention member 20 is preferably made of a crystalline resin since it is relatively large and does not require high positioning precision in the analysis apparatus 1. A crystalline resin is also preferred in terms of resistance to test reagents and cost. Also with this configuration, it is possible to suppress the production cost.

EXAMPLES (1) Sample Preparation
(1.1) Sample 1
Test Reagent Retention Member
A test reagent retention member having the same configuration as illustrated in FIG. 1 and FIG. 2A was produced.

The material of the test reagent retention member is preferably a crystalline resin since it requires resistance to test reagents.

Figure 12A:
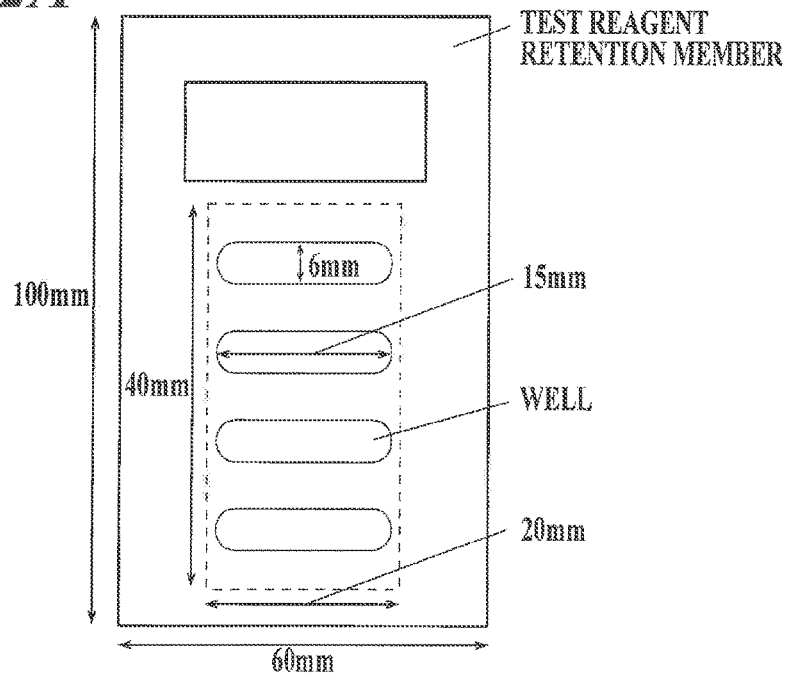
FIG. 12A is a plan view of a test reagent retention member of Sample 1.

In this sample, the test reagent retention member was produced from PP by injection molding and had the size as illustrated in FIG. 12A. The test reagent retention member had a thickness of 15 mm and a well depth of 10 mm.

Thereafter, test reagent was dispensed in the wells, and the wells were sealed with an Al sheet in order to prevent leakage of the test reagent. The sealing was achieved by thermal fusion.

Figure 12B:
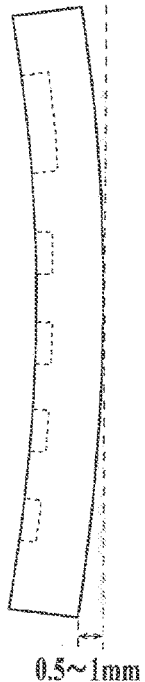
FIG. 12B is a side view of the test reagent retention member of Sample 1.

As illustrated in FIG. 12B, the warpage of the test reagent retention member after the sealing was from 0.5 mm to 1 mm.

Sensing Member
A sensing member having the same configuration as illustrated in FIG. 3A to FIG. 3D was produced.

Since the sensing member has to be transparent, the material thereof is preferably a non-crystalline resin.

Figure 13A:
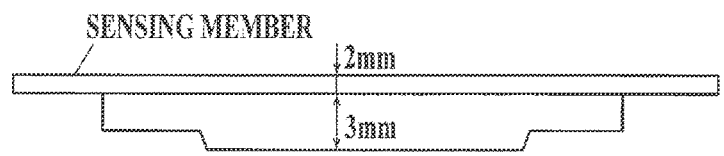
FIG. 13A is a side view of a sensing member of Sample 1.
Figure 13B:
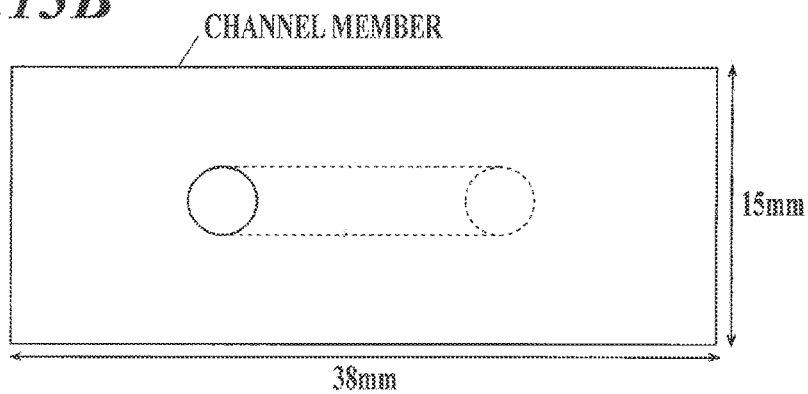
FIG. 13B is a plan view of a channel member of Sample 1.
Figure 13C:
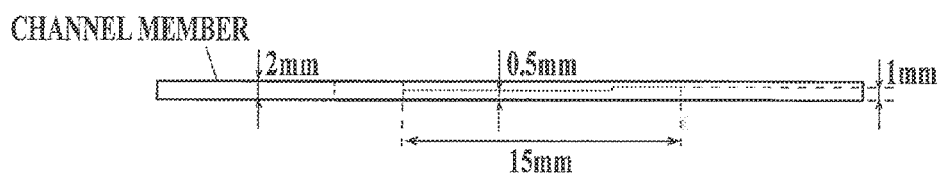
FIG. 13C is a side view of the channel member of sample 1.
Figure 13D:
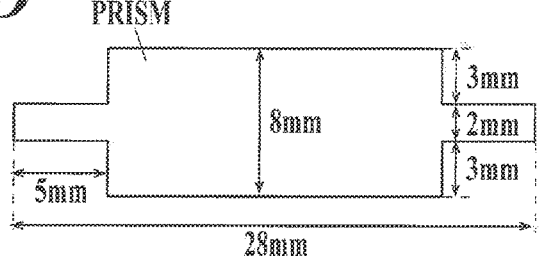
FIG. 13D is a plan view of a prism of Sample 1.
Figure 13E:
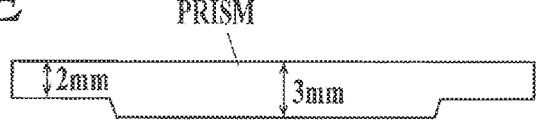
FIG. 13E is a side view of the prism of Sample 1.

In this sample, a channel member was produced from PMMA (polymethyl methacrylate) by injection molding and had the size as illustrated in FIG. 13A to FIG. 13C. A prism was produced from COP (cycloolefin polymer, E48R of ZEON Corporation) by injection molding and had the size as illustrated in FIG. 13A, FIG. 13D and FIG. 13 E.

Thereafter, an Au film was formed to a thickness of 50 nm on the entire top face of the prism by sputtering, and a circular immobilized membrane (antigen protein) is formed on the Au film. The prism member was thus produced. The immobilized membrane was formed in an area with 5 mm diameter.

Thereafter, the channel member was joined with the prism member so that the reaction channel was formed. The sensing member was thus produced.

Assembly of Analysis Chip

The sensing member is integrated with the test reagent retention member in a snap-fitting manner.

The movable areas or the engaging distances as described with reference to FIG. 5A and FIG. 5B were Sk=0.05 mm, A=0.4 mm and Tk=0.6 mm.

(1.2) Sample 2 to Sample 13

The movable areas and the engaging distances in Sample 1 were changed as listed in Table 1.

(1.3) Sample 14

Figure 14:
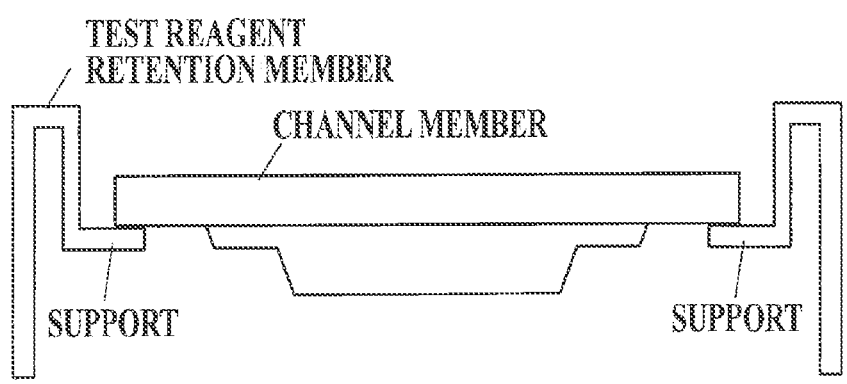
FIG. 14 illustrates the integration of a test reagent retention member with a sensing member of Sample 14.

The hooks of the test reagent retention member in Sample 1 were not formed intentionally. In assembling the analysis chip, the channel member is bonded to the supports of the test reagent retention member by thermal bonding as illustrated in FIG. 14 so that no movable area is formed.

(2) Sample Evaluation (2.1) Evaluation of Integration

Each sample was rotated by 360° to all directions, and it was checked whether the test reagent retention member was integrated with the sensing member without causing separation.

The test results are shown in Table 1. The evaluation criteria are as follows.

○: Integrated without causing separation
x: Separation was caused.

(2.2) Positioning Precision

A stage and a presser member having the same configuration as illustrated in FIG. 10A to FIG. 10C were prepared.

As described with reference to FIG. 11A to FIG. 11C, each sample was placed on the stage, and the presser member is placed thereon and was set on the stage. In this condition, the deviation of the sensing member from the reference position in the height direction and the front-rear direction was checked.

The test results are shown in Table 1. The evaluation criteria are as follows.

○: ±50 μm or less
x: More than ±50 μm

TABLE 1

| SAMPLE | TYPE OF INTEGRATION | Sk (mm) | A (mm) | Tk (mm) | INTEGRATION | POSITIONING ACCURACY OF ±50 μm OR LESS HEIGHT DIRECTION | FRONT-REAR DIRECTION |
|---|---|---|---|---|---|---|---|
| 1 | SNAP-FITTING TYPE (WITH MOVABLE AREA) | 0.05 | 0.4 | 0.6 | ○ | ○ | ○ |
| 2 | SNAP-FITTING TYPE (WITH MOVABLE AREA) | 0 | 0.4 | 0.6 | ○ | x | ○ |
| 3 | SNAP-FITTING TYPE (WITH MOVABLE AREA) | 0.6 | 0.4 | 0.6 | x | x | x |
| 4 | SNAP-FITTING TYPE (WITH MOVABLE AREA) | 0.2 | 0.4 | 0.6 | ○ | ○ | ○ |
| 5 | SNAP-FITTING TYPE (WITH MOVABLE AREA) | 0.3 | 0.4 | 0.6 | ○ | ○ | ○ |
| 6 | SNAP-FITTING TYPE (WITH MOVABLE AREA) | 0.05 | 0.8 | 0.6 | x | x | x |
| 7 | SNAP-FITTING TYPE (WITH MOVABLE AREA) | 0.05 | 0.05 | 0.6 | x | x | x |
| 8 | SNAP-FITTING TYPE (WITH MOVABLE AREA) | 0.05 | 0.15 | 0.6 | ○ | ○ | ○ |
| 9 | SNAP-FITTING TYPE (WITH MOVABLE AREA) | 0.05 | 0.65 | 0.6 | ○ | ○ | ○ |
| 10 | SNAP-FITTING TYPE (WITH MOVABLE AREA) | 0.05 | 0.4 | 0 | ○ | x | ○ |
| 11 | SNAP-FITTING TYPE (WITH MOVABLE AREA) | 0.05 | 0.4 | 1.2 | x | x | x |

TABLE 1-continued

| SAMPLE | TYPE OF INTEGRATION | Sk (mm) | A (mm) | Tk (mm) | INTEGRATION | POSITIONING ACCURACY OF ±50 μm OR LESS | |
|---|---|---|---|---|---|---|---|
| | | | | | | HEIGHT DIRECTION | FRONT-REAR DIRECTION |
| 12 | SNAP-FITTING TYPE (WITH MOVABLE AREA) | 0.05 | 0.4 | 0.04 | ○ | ○ | ○ |
| 13 | SNAP-FITTING TYPE (WITH MOVABLE AREA) | 0.05 | 0.4 | 0.9 | ○ | ○ | ○ |
| 14 | THERMAL BONDING (WITHOUT MOVABLE AREA) | — | — | — | ○ | x | x |

As illustrated in Table 1, good evaluation results were given in Sample 1, Sample 4, Sample 5, Sample 8, Sample 9, Sample 12 and Sample 13.

In contrast, in Sample 2, the position was largely deviated since the sensing member was not movable enough to finely adjust the height position due to the too small movable areas Sk. In Sample 3, the sensing member is detached from the test reagent retention member due to the excessive movable areas Sk, and integration and positioning were not able to be carried out.

In Sample 6, the engaging parts of the test reagent retention member were broken due to the excessive engaging distance A, and integration and positioning were not able to be carried out. In Sample 7, the sensing member was detached from the test reagent retention member due to the too small engaging distance A, and integration and positioning were not able to be carried out.

In Sample 10, the position was largely deviated since the sensing member was not movable due to the too small movable areas Tk. In Sample 11, the test reagent retention member was separated from the sensing member due to the excessive movable areas Tk, and integration and positioning were not able to be carried out.

In Sample 14, the position was largely deviated in the front-rear direction and the height direction since there was a considerable influence of the warpage of the test reagent retention member.

In view of the foregoing, it was found that employing the snap-fitting method and satisfying the conditions of the expressions (1) and (2) for the movable areas Sk, Tk are effective for preventing separation of the test reagent retention member from the sensing member and improving the positioning precision of the sensing member to a level of 50 μm or less.

INDUSTRIAL APPLICABILITY

The present invention, which relates to an analysis chip that is used for SPR, is suitably applicable particularly for improving the positioning precision of a sensing member.

REFERENCE SIGNS LIST

1. Analysis apparatus
10 Analysis chip
20 Test reagent retention member
22 Well
24 Housing part
26 Sealing member
30 Sensing member
40 Channel member
42 Test reagent introduction part
44 Reaction channel
50 Prism member
52 Prism
54 Metal film
56 Immobilized membrane
60 Engaging part
62 Inner wall
64 Support
66 Hook
100 Stage
102 Housing part
104, 106 Protrusion
108 Plunger
112 Protrusion
200 Presser member
202 Bottom part
204 Top plate part

The invention claimed is:

1. An analysis chip for analysis using principle of surface plasmon resonance, comprising:
    a test reagent retention member; and
    a sensing member,
    where a test reagent retention member comprises:
        a housing part in which the sensing member is housed; and
        an engaging part which engages with the sensing member in the housing part, the engaging part forming a snap-fit connection between the sensing member and the test reagent retention member, and
    wherein the sensing member is housed in the housing part by means of the engaging part with a certain movable area between the sensing member and the housing part.

2. The analysis chip according to claim 1, wherein the test reagent retention member and the sensing member are made of different materials.

3. The analysis chip according to claim 2, wherein the test reagent retention member and the sensing member are made of different resins, and wherein the sensing member is made of a resin that has better shape and dimension precision than a resin of the test reagent retention member.

4. The analysis chip according to claim 3,
wherein the test reagent retention member is made of a crystalline resin, and
wherein the sensing member is made of a non-crystalline resin.

5. The analysis chip according to claim 1,
wherein a movable area Sk in a width direction between the housing part and the sensing member satisfies a condition of expression (1).

$$0.01mm \leq Sk \leq 0.58mm \quad (1)$$

6. The analysis chip according to claim 1,
wherein a movable area Tk in a height direction between the housing part and the sensing member satisfies a condition of expression (2).

$$0.01mm \leq Tk \leq 1mm \quad (2)$$

7. The analysis chip according to claim 1,
wherein the engaging part is made of an elastic material.

8. The analysis chip according to claim 1,
wherein the engaging part is of a spring type and is made of any one of a resin, a metal and a ceramic.

9. The analysis chip according to claim 1,
wherein the engaging part is of a press-fitting type.

10. An analysis apparatus, comprising:
the analysis chip according to claim 1;
a stage on which the analysis chip is placed; and
a positioning member which positions the sensing member of the analysis chip.

11. The analysis chip according to claim 1,
wherein the engaging part includes a hook that protrudes from an inner wall on the housing part.

12. The analysis chip according to claim 1,
wherein the engaging part includes hooks arranged on opposing sides of the housing part.

13. The analysis chip according to claim 1,
wherein the engaging part includes at least one hook and at least one support protruding from an inner wall on the housing part, and the sensing member is held between the at least one support and the at least one hook when the sensing member is housed in the housing part.

* * * * *